US00PP14849P2

(12) United States Plant Patent
Brljevich et al.

(10) Patent No.: US PP14,849 P2
(45) Date of Patent: Jun. 1, 2004

(54) CALLA LILY PLANT NAMED 'ROMEO'

(50) Latin Name: *Zantedeschia sprengeri*
Varietal Denomination: Romeo

(75) Inventors: Trevor Brljevich, Maungaturoto (NZ); Yvonne Brljevich, Maungaturoto (NZ)

(73) Assignee: Pukekaroro Exotics Ltd. (NL)

( * ) Notice: Subject to any disclaimer, the term of this patent is extended or adjusted under 35 U.S.C. 154(b) by 0 days.

(21) Appl. No.: 10/638,655

(22) Filed: Aug. 11, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Webb Zesenheim Logsdon Orkin & Hanson, P.C.

(57) ABSTRACT

'Romeo' is a new variety of calla lily having beautiful waxy burgundy-red colored spathes.

4 Drawing Sheets

Botanical classification: *Zantedeschia sprengeri.*
Varietal denomination: 'Romeo'.

BACKGROUND OF THE NEW PLANT

The present invention comprises a new and distinct cultivar of calla lily, botanically known as *Zantedeschia sprengeri* and hereinafter referred to by the cultivar name 'Romeo'.

'Romeo' was discovered in 1996 and chosen from a selection of seedling tubers of unknown parentage in Maungaturoto, New Zealand. The first act of asexual reproduction of 'Romeo' by tissue culture was performed in 1997 in Auckland, New Zealand. Subsequent asexual reproductions by tissue culture have demonstrated that the combination of characteristics as herein disclosed for the new cultivar are retained through successive generations of asexual reproduction.

The following traits have been repeatedly observed and determined to be basic characteristics of 'Romeo' which, in combination, distinguish this calla lily as a new and distinct cultivar:

1. 'Romeo' has a different shaped leaf with fewer leaf maculations than 'Majestic Red' (unpatented) and 'Pink Persuasion' (unpatented);
2. 'Romeo' is taller than 'Majestic Red' (unpatented);
3. 'Romeo' is more burgundy red than 'Dominique' (unpatented), 'Chianti' (unpatented), and 'Carmine Red' (unpatented); and
4. 'Romeo' is taller with a larger spathe than 'Neon Armour' (unpatented) and 'Garnet Glow' (unpatented).

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
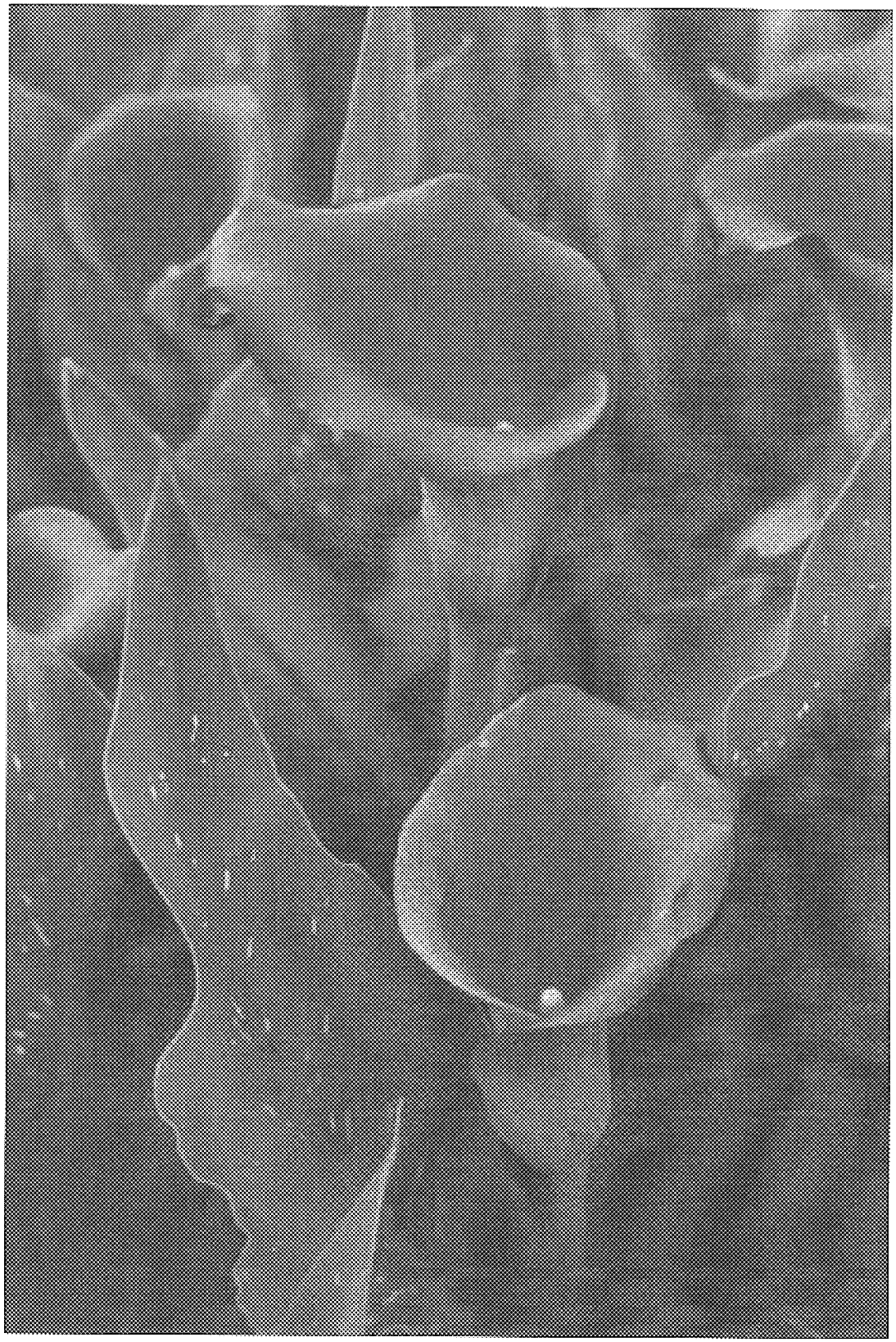
FIG. 1 is a close-up photograph of inflorescences of the new variety.
Figure 2:
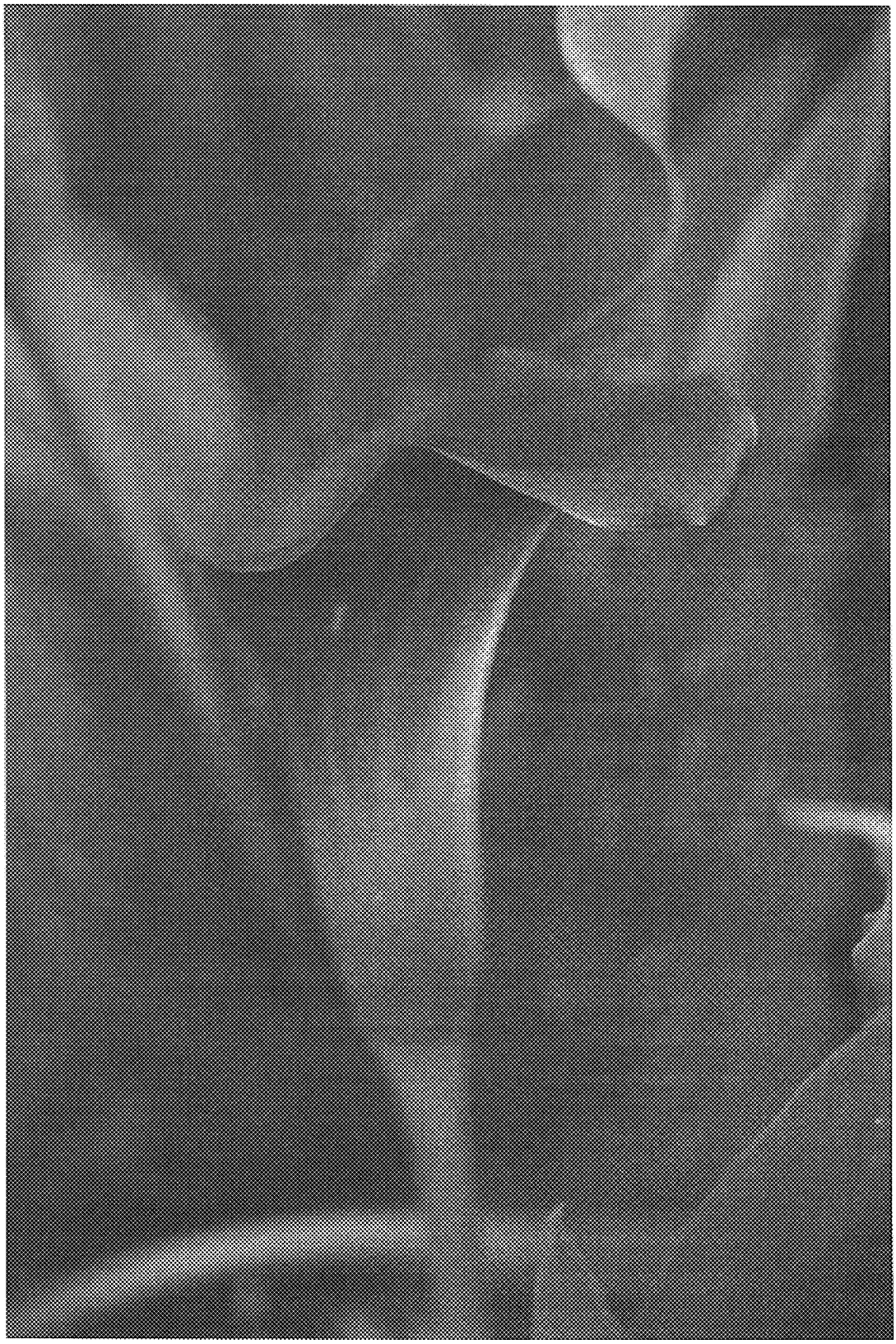
FIG. 2 is a close-up photograph of a single inflorescence of the new variety.
Figure 3:
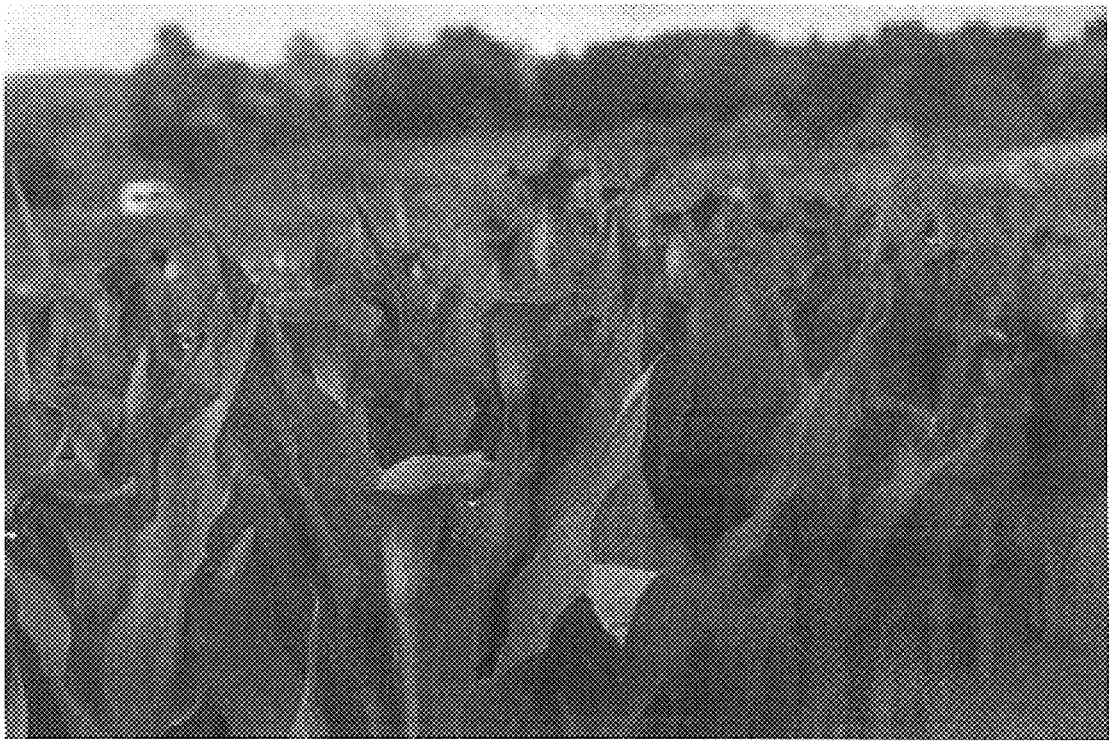
FIG. 3 is a photograph of a field of the new variety.
Figure 4:
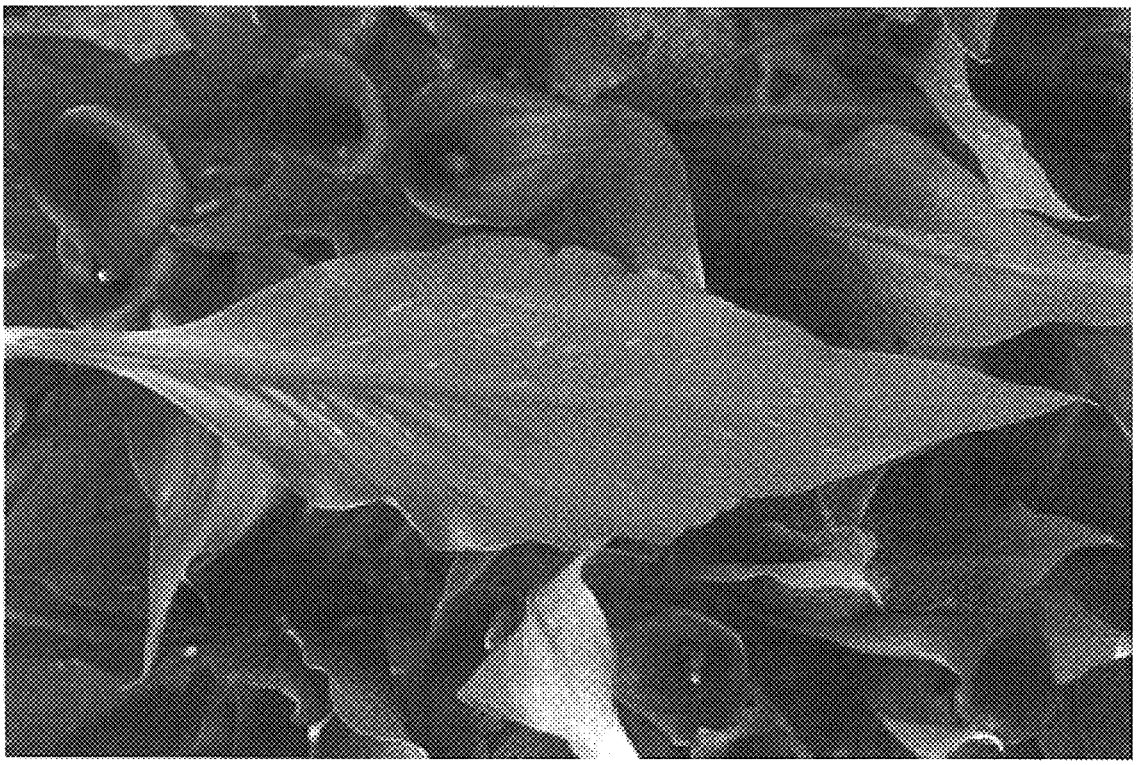
FIG. 4 is a close-up photograph of a leaf of the new variety.

The following observations, measurements, and comparisons describe plants grown in New Zealand under conditions which approximate those generally used in horticulture practice. Plants described were 14 weeks from planting date of tuber. Color references are made to The R.H.S. Colour Chart of The Royal Horticultural Society of London, except where general color terms of ordinary significance are used.

THE PLANT

Size:
- *Height of the leaf canopy above the soil.*—500–750 mm; Average of 600 mm.
- *Height of top of flowers above the soil.*—300–700 mm; Average of 550 mm.
- *Diameter.*—250–400 mm; Average of 350 mm.
- *Form*—Erect.

Number of inflorescences per tuber size:
- *Diameter of 3–4 cm.*—2–4 flowers.
- *Diameter of 4–5 cm.*—3–10 flowers.
- *Diameter of 5–6 cm.*—8–14 flowers.

Branches:
- *Character.*—Strong.
- *Color.*—147A.
- *Number.*—1–8 per plant.

Leaves:
- *Size.*—Width: 80–120 mm; Average of 100 mm. Length: 200–350 mm; Average of 310 mm.
- *Shape.*—Lanceolate to ovate.
- *Number per plant.*—10–35.
- *Color.*—Upper surface: 147A to 147B. Lower surface: 147A to 147B.
- *Spotting or mottling.*—Description: 40–70 maculations per leaf, ranging from 1 mm dots to 10 mm long×1 mm wide lines. Color: Transparent.
- *Margin.*—Very fine; colored 154A to 154B to 154C and 154D.
- *Veins.*—Configuration: Pinnate. Color: 144C.
- *Surface quality.*—Leathery.

Petiole:
- *Length*—200–450 mm.
- *Color*—144C with striations of 144A.

Roots:
- *Color.*—White.
- *Branching.*—Moderate, average.

THE INFLORESCENCE

Spathe:

*Size.*—Length: 70–120 mm; Average of 100 mm. Width: 40–60 mm; Average of 55 mm.

*Color.*—Inner surface: Base of spathe is 79A to 79B, changing to 59A to 59B or 187B to 187C toward the apex. Outer surface: Background color at base of spathe is 85B to 85C, with an overlay of 59A to 59B to 59C at the outer edge of the spathe.

*Veins.*—Color: 79A to 79B changing to 59A toward the rim (outer edge) of the spathe. Configuration: Parallel.

*Shape.*—Overall: Cupped. Tip: Reflexed. Base: Cylindrical and widening distally.

Spadix:

*Size.*—Length: 30–60 mm; average of 55 mm. Diameter: 5–8 mm.

*Color.*—Male organs: 13B to 13C. Female organs: 3D, with faint speckling of 79A.

*Position relative to spathe.*—Upright.

Peduncle:

*Size.*—Length: 400–600 mm; Average of 450 mm. Diameter: 7–10 mm.

*Color.*—144D with striations of 144B to 144C.

Reproductive organs:

*Location of female organs.*—Basal position of the spadix (lower 35%).

*Location of male organs.*—Upper position of the spadix (upper 65%).

*Perianth.*—Conspicuous.

*Stamens.*—Visible before pollen release.

*Number per spadix.*—Between 12 to 30.

*Pistil.*—Length beyond perianth: 0.5 mm. Shape: Dome.

Flowering: Tubers planted in New Zealand begin to produce inflorescences 85 days after planting and continue to flower over a 20–30 day period.

Disease/pest resistance: Relatively resistant to most diseases and pests which can affect Zantedeschia.

Lastingness: Cut flowers last 5–14 days.

Fragrance: None.

We claim:

1. A new and distinct variety of calla lily plant named 'Romeo' as described and illustrated.

* * * * *